US007331251B2

(12) United States Patent
Das et al.

(10) Patent No.: US 7,331,251 B2
(45) Date of Patent: Feb. 19, 2008

(54) DISSOLUTION TESTING OF SOLID DOSAGE FORMS INTENDED TO BE ADMINISTERED IN THE ORAL CAVITY

(75) Inventors: Nandita G. Das, Carmel, IN (US); Sudip K. Das, Carmel, IN (US); Madhu S. Surapaneni, Wheeling, IL (US)

(73) Assignee: Idaho State University, Pocatello, ID (US)

( * ) Notice: Subject to any disclaimer, the term of this patent is extended or adjusted under 35 U.S.C. 154(b) by 214 days.

(21) Appl. No.: 11/158,903

(22) Filed: Jun. 22, 2005

(65) Prior Publication Data

US 2006/0288805 A1 Dec. 28, 2006

(51) Int. Cl.
  *G01N 33/00* (2006.01)
  *G01N 33/15* (2006.01)
(52) U.S. Cl. .................................................. 73/866
(58) Field of Classification Search .............. 73/866, 73/865.6, 866.4
See application file for complete search history.

(56) References Cited

U.S. PATENT DOCUMENTS

| | | | | |
|---|---|---|---|---|
| 3,791,222 A | * | 2/1974 | Goodhart et al. | .............. 73/866 |
| 3,802,272 A | * | 4/1974 | Bischoff et al. | .............. 73/866 |
| 4,247,298 A | * | 1/1981 | Rippie | .............. 73/866 X |
| 4,279,860 A | * | 7/1981 | Smolen | .............. 73/866 X |
| 5,127,278 A | * | 7/1992 | Benz | .............. 73/866 |
| 5,142,920 A | * | 9/1992 | Bart et al. | .............. 73/866 |
| 5,412,979 A | * | 5/1995 | Fassihi | .............. 73/866 X |
| 5,639,974 A | | 6/1997 | Hanson et al. | |
| 5,807,115 A | | 9/1998 | Hu | |
| 6,004,822 A | | 12/1999 | Li et al. | |
| 6,060,024 A | | 5/2000 | Hutchins et al. | |
| 6,163,149 A | * | 12/2000 | Loffler | .............. 73/866 X |
| 6,170,980 B1 | * | 1/2001 | Martin | .............. 73/866 X |
| 6,799,123 B2 | | 9/2004 | Hughes | |
| 6,948,389 B2 | | 9/2005 | Brinker et al. | |
| 7,024,955 B2 | * | 4/2006 | Carlson et al. | .............. 73/866 |
| 2002/0061540 A1 | * | 5/2002 | Grass et al. | .............. 435/7.1 |
| 2003/0087457 A1 | | 5/2003 | Hughes | |
| 2003/0235110 A1 | | 12/2003 | Qureshi | |
| 2005/0123601 A1 | * | 6/2005 | Mane et al. | .............. 424/451 |
| 2006/0134195 A1 | * | 6/2006 | Fu et al. | .............. 424/464 |

FOREIGN PATENT DOCUMENTS

| | | | | |
|---|---|---|---|---|
| DE | 2942129 A | * | 4/1981 | |
| JP | 63230077 | * | 9/1988 | .............. 435/283.1 |

OTHER PUBLICATIONS

Das et al. (2004) "Development of Mucoadhesive Dosage Forms of Buprenorphine for Sublingual Drug Delivery," *Drug Deliv.* 11:89-95.

(Continued)

*Primary Examiner*—Thomas P. Noland
(74) *Attorney, Agent, or Firm*—Greenlee, Winner and Sullivan, P.C.

(57) ABSTRACT

The invention is a method and device for determining dissolution of a solid compound within the oral cavity. The device models dissolution within the oral cavity with a flow-through cell containing a solid compound and physiological amounts of simulated saliva. The device supplies and removes the simulated saliva at rates similar to production and loss of saliva within the oral cavity. The simulated saliva interaction with the solid compound mimics saliva interaction with a solid compound within the oral cavity. Dissolution of solid compound is determined from simulated saliva collected from the flow-through cell outflow.

19 Claims, 2 Drawing Sheets

OTHER PUBLICATIONS

Tan et al. (2000) "Effect of Carbopol and Polyvinylpyrrolidone on the Mechanical, Rheological, and Release Properties of Bioadhesive Polythylene Glycol Gels," *AAPS PharmSciTech* 1(3):article 24 10 pages.

Varian, Inc. (2004) "Direct Vessel Heating System (DVH)," *Dissolution Systems Application Note PN* 74-2000 1-3 May 2004.

Varian Inc. "VK 7030 Dissolution Tester," 74-1074, Rev. A, 1-2 by Oct. 2005.

* cited by examiner

DISSOLUTION TESTING OF SOLID DOSAGE FORMS INTENDED TO BE ADMINISTERED IN THE ORAL CAVITY

STATEMENT REGARDING FEDERALLY SPONSORED RESEARCH OR DEVELOPMENT

This invention was made, at least in part, with government support under 1R15DA015358-01 awarded by the National Institute on Drug Abuse. The government has certain rights in the invention.

CROSS-REFERENCE TO RELATED APPLICATIONS

Not Applicable.

FIELD OF INVENTION

This invention generally relates to a method and apparatus for in vitro evaluation of dissolution of solid dosage forms in the oral cavity, including the buccal and sublingual environments.

BACKGROUND OF THE INVENTION

Administration of pharmaceuticals and other solid formulations via absorption in the oral cavity provide several advantages over administration via absorption from the gastrointestinal (GI) tract. Buccal (against the cheek) and sublingual (under the tongue) dosage forms of drugs can bypass first-pass metabolism that occurs in the intestine during absorption and in the liver immediately following absorption from the GI tract. Such first-pass metabolism results in reduction of available drug material. In addition, drug absorption in the oral cavity can result in a rapid onset of drug action because the oral cavity has a rich supply of blood vessels to transport the drug throughout the systemic circulatory system. Therefore, buccal/sublingual dosage forms can provide more biologically available drug and adequate plasma levels of a drug at lower initial administration dosage compared to drugs delivered via administration from the GI tract. Drugs absorbed within the oral cavity also are delivered systemically faster than drugs absorbed from the GI tract. In order to determine appropriate dosing for drug delivery via the oral cavity, it is important to quantify the time course of a drug's dissolution within the oral cavity. There is need in the art for devices that simulate the flow of saliva in the human mouth and the subsequent dissolution of drugs in the oral cavity. The present invention provides improved methods and apparatus for determining, in vitro, the dissolution of a solid compound placed within the oral cavity.

A number of sublingual dosage forms are available for pain control, heart conditions, asthma, antiemesis and treatment of drug abuse including, for example, nitroglycerine, subutex, suboxone and isoproterenol. Because of the advantages outlined above, further increase in formulations utilizing sublingual dosage forms is expected. An oral delivery route is a non-invasive means to deliver a wide variety of biotechnological or pharmaceutical products including, for example, proteins, peptides, oligonucleotides, siRNA and gene therapy compositions.

There are numerous in vitro apparatuses for testing dissolution of formulations in the gastro-intestinal (GI) tract. See, e.g. U.S. Pat. Nos. 5,639,974, 5,807,115, 6,060,024; U.S Pat. Pub. No. 2003/0235110; The United States Pharmacopeial Convention, USP 25. However, these systems are not suitable for assessing dissolution of solid formulations in the oral cavity. First, the GI apparatuses typically contain up to 900 mL of solution, agitated using either a paddle stirrer or a rotating basket assembly. For stirrer assemblies, the stirrer must be completely submerged in the dissolution fluid. Therefore, the minimum amount of fluid with which the dissolution vessel can be operable is about 450 mL. USP 25 recommends using 900 mL fluid for most studies. The fluid capacity and/or content of the human mouth is much less than 900 mL or even the minimum volume of 450 mL. In addition, the paddle and rotating basket-type assemblies produce considerable agitation of the dissolution medium. Such agitation suitably models peristaltic movement in the GI tract. However, because the oral cavity lacks peristaltic movement, such agitation is inappropriate for simulating dissolution within the oral cavity.

The fluid dynamics of the apparatuses that model GI-tract dissolution are also inappropriate for modeling dissolution within the oral cavity. Such GI apparatuses are closed systems in that the dissolution medium does not continuously enter and leave the vessel. Generally, samples are withdrawn from the vessel at different time intervals and the vessel contents may or may not be replenished by fresh medium. The samples are then analyzed for drug content to determine the rate and extent of dissolution. Such systems may be adequate for modeling dissolution within the GI tract, and especially the stomach cavity, where fluid turnover is minimal. Saliva, in contrast, is produced and swallowed continuously so that a closed vessel design does not accurately simulate the oral cavity.

Hughes (U.S. Pat. Pub. No. 2003/0087457) addresses dissolution of compounds in the buccal cavity prior to passage to the GI. The apparatus in Hughes suffers a drawback in that the interaction of dissolution medium with the solid compound does not realistically model dissolution of the solid in the oral cavity where all surfaces of the solid compound are exposed to dissolution fluid flow. In addition, the apparatus in Hughes is a relatively complex and expensive means for assessing dissolution comprising two outlet ports and an in-line dissolution analyzer. In addition, the dissolution medium is stirred, which inappropriately simulates the relatively gentle fluid movements in the oral cavity and requires larger dissolution fluid volumes to ensure immersion of the stirrer.

Li et al. (U.S. Pat. No. 6,004,822) describe a device to measure dissolution of solids in submilliliter quantities (10 to 400 microliters) of a solvent and correspondingly small amount of the solid. The device in Li unsatisfactorily models dissolution in the oral cavity because, in part, there is no flow-through cell, but rather it is a closed system. The solvent remains within the cell and is pumped between two chambers in fluid communication with one another. The oral cavity, in contrast, contains approximately 50 mL of saliva that is continuously replenished as saliva exits the oral cavity or is absorbed and/or broken down during solid dissolution.

BRIEF SUMMARY OF THE INVENTION

The invention provides devices and methods for assessing dissolution of solid compounds within the oral cavity. In one embodiment, the invention is a device comprising an influx source and efflux sink, each connected to a flow-through cell that holds a volume of dissolution medium and in which a solid sample can be disposed. The source and sink have a dissolution medium inflow flow-rate and efflux flow-rate, respectively, so that the flow-through cell has a continuous turnover of dissolution medium to simulate the production and removal of saliva within the oral cavity. A solid compound can be placed on a sample holder disposed within the flow-through cell so that dissolution of the compound can be measured as a function of time under physical conditions that mimic the conditions within the oral cavity. A filter is disposed between the flow-through cell and the efflux sink so that undissolved compound is prevented from entering the efflux sink and instead remains within the flow-through cell. A temperature controlled adjustable rocker-assembly is connected to the flow-through cell to rock the flow-through cell at a user-controlled temperature, thereby modeling the gentle movement of saliva within the oral cavity. The rocking can be rate controllable. Alternatively, the rocker can have a constant rock rate, ranging from between 15 and 35 complete movements per minute, and more preferably approximately 25 complete movements per minute.

The influx source and efflux sink encompass any means to continuously supply and remove liquid medium to and from the flow-through cell. Influx source and efflux sink includes tubing and associated dissolution fluid reservoirs, as well as means for generating fluid flow. Means for generating fluid flow can be a pump or a pressure head. The fluid reservoir can be contained within the volume of a syringe pump. In a further embodiment, the magnitude of the inflow flow-rate, the efflux flow-rate, or both the inflow and outflow flow-rates can be controlled. The inflow and efflux flow-rates can be independently controlled via separate flow-rate controls. In a preferred embodiment, the inflow and efflux flow-rates are equivalent, within the accuracy of the flow generating means (e.g. ±10%).

Using similitude and modeling principles, the flow-through cell can contain a desired volume of dissolution medium. In one embodiment, the flow-through cell contains less than 100 mL of dissolution medium, thereby simulating the volume of saliva fluid that is typically found within the oral cavity. The flow-rates into and out of the flow-through cell are constrained by the volume of dissolution medium contained within the flow-through cell. In one embodiment, wherein less than 100 mL of fluid is contained within the flow-through cell, the inflow flow-rate is less than 2 mL/min, and more preferably between 0.8-1.2 mL/min, and most preferably approximately 1 mL/min.

In another embodiment, the device further comprises a collection device for collecting a sample of dissolution medium within the efflux sink. Because the efflux sink is downstream of the filter, the sample does not contain a measurable quantity of undissolved particles. The amount of dissolved compound within the sample can then be measured by means known in the art. Repeating such measurements over time permits a dissolution time course to be obtained. The collection device is any means known in the art for collecting a volume of fluid including, for example, a user collecting a sample from the efflux reservoir, a separate sample line connected to the outflow tubing, a syringe connected to a stopcock within the outflow tubing, or a separate pump for generating a collection sample flow rate from the outflow tubing.

Another embodiment for the device comprises a flow-through cell for receiving a volume of dissolution medium and for holding a compound comprising inflow and outflow ports and a compound holder. An inflow means is connected to the inflow port for introducing dissolution medium to the flow-through cell and an outflow means is connected to the outflow port for removing dissolution medium from the flow-through cell. The inflow and/or outflow means can be a pump or a fluid reservoir wherein flow is generated by the height difference between the dissolution medium contained within the inflow reservoir and the medium contained within the efflux reservoir or flow-through cell. Flow means also includes, in addition to pumps and/or reservoirs, associated tubing, fittings and other components associated with providing and regulating flow, such as flowmeters and/or valves. The outflow and inflow ports are the location at which the outflow and inflow tubing, respectively, connect for inflow to, and outflow from, the flow-through cell. The movement of saliva within the oral cavity is modeled by a rocker assembly that rocks the flow-through cell to simulate saliva interaction with solid compound in the oral cavity, so that dissolved compound is uniformly mixed within the dissolution medium disposed within the flow-through cell. In a further embodiment, a collection device is connected to the outflow means for collecting a sample of dissolution medium. The collection device can comprise an efflux reservoir, tubing, and/or any other equipment for collecting a volume of liquid, as known in the art.

Undissolved compound can be prevented from entering the collection device by placing a filter upstream from the collection device. In one embodiment, the filter is disposed within the outflow port.

In another embodiment the device further comprises a temperature-controlled assembly connected to the flow through cell and/or inflow reservoir. In a preferred embodiment, the temperature of the dissolution medium within the flow-through cell is maintained at approximately 37° C. The flow-through cell is designed to hold a volume of dissolution medium. In an embodiment this volume is less than 100 mL. Preferably the volume is between 35 mL and 75 mL. The dissolution medium can be any fluid of interest in which the dissolution of a solid compound is to be determined. The medium can be water. In a preferred embodiment the medium is a simulated saliva.

The invention also provides a method for determining the dissolution of a solid compound using any of the devices of the present invention by placing a solid compound on the compound holder of the device, supplying dissolution medium to the flow-through cell, collecting a sample of dissolution medium from the efflux sink and analyzing the sample to determine the dissolution of the solid compound. A dissolution time course can be obtained by repeatedly collecting samples at various times after initiating flow to the flow-through cell containing solid compound. The time between collecting samples depends on the rate of dissolution, with faster dissolution rates dictating higher collection frequency. Frequency of sample collection can range from on the order of tens of seconds to tens of minutes to obtain a sufficiently accurate dissolution time course. Alternatively, the outflow tubing associated with the efflux sink can be connected to an in-line dissolution analyzer to continuously measure dissolution as a function of time. The duration of the dissolution time course depends on the dissolution properties of the solid compound, with the time course ending when the solid compound has dissolved.

DETAILED DESCRIPTION OF THE INVENTION

The invention may be further understood by the following non-limiting examples. All references cited herein are hereby incorporated by reference to the extent not inconsistent with the disclosure herewith. Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given.

Whenever a range is given in the specification, for example, a temperature range, a time range, a flow-rate range, or a size range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The following definitions are provided to clarify their specific use in the context of the invention.

Figure 1:
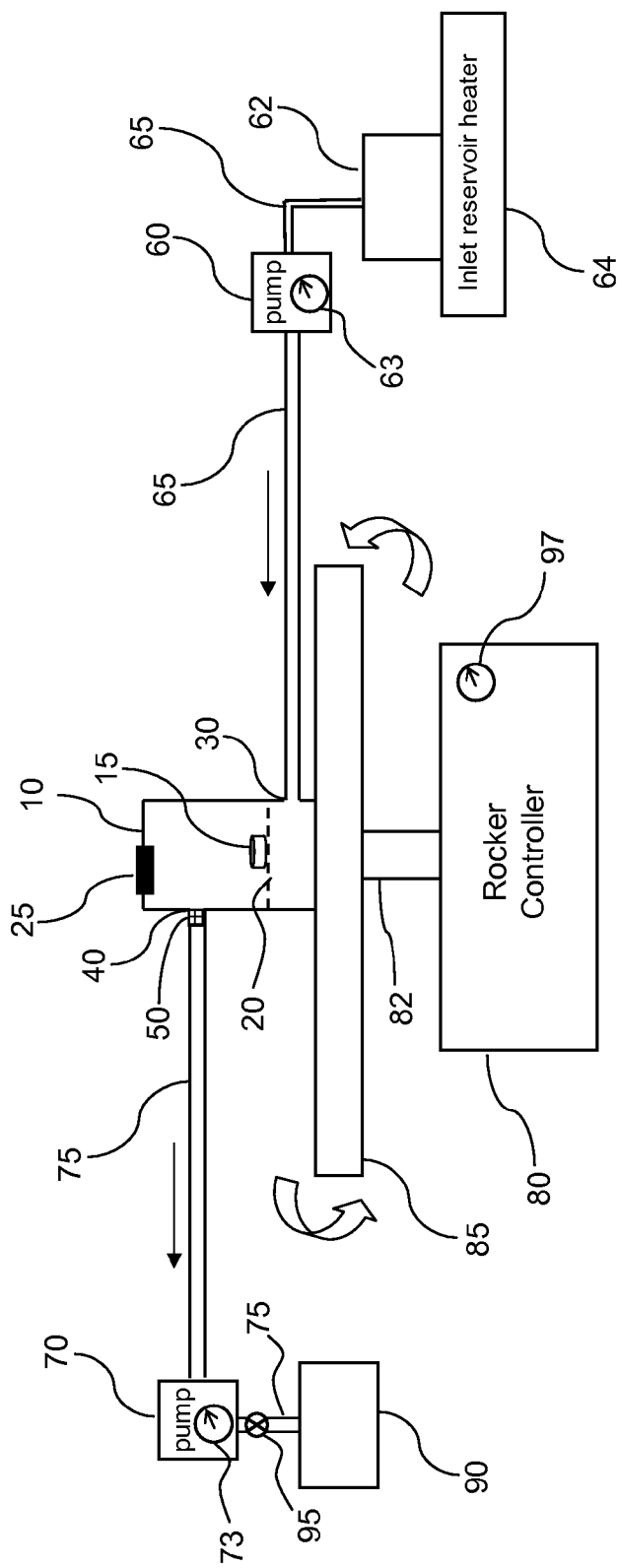
FIG. 1: Schematic illustration of a dissolution apparatus that simulates dissolution of a solid compound within the oral cavity.

FIG. 1 shows one embodiment of an apparatus to simulate dissolution of a solid compound in the oral cavity of an animal. In a preferred embodiment, the oral cavity that is simulated is a human oral cavity. A solid compound 15 whose dissolution characteristics are to be determined is disposed within a flow cell 10. Dissolution medium flows into the flow-through cell 10 via an inflow port 30 and exits the flow-through cell via an outflow port 40. The compound 15 is placed on a compound holder 20 to facilitate flow of dissolution medium over all surfaces of compound 15, thereby modeling saliva interaction with a solid compound within the oral cavity where saliva can interact with all exposed solid compound surfaces. In an embodiment the compound holder 20 is a mesh upon which compound 15 is placed. Dissolution medium is provided to the flow-through cell inflow port 30 by inflow means. In the embodiment shown in FIG. 1, inflow means comprises inflow tubing 65, pump 60 and inlet reservoir 62. The inlet reservoir is optionally maintained at a user-controlled temperature by inlet reservoir heater 64. Inflow means is any means known in the art that provides fluid delivery and can be a pump 60 and associated inflow tubing 65. Alternatively, the fluid can be gravity driven with flow rate controlled by varying the flow head of an inlet fluid reservoir and/or by controllable valves. Dissolution medium is removed from the flow-through cell via outflow port 40 by efflux means. Efflux means is any means known in the art to remove fluid and can be a pump 70, associated outflow tubing 75, and efflux reservoir 90. Alternatively, the fluid can be removed by a passive gravitational system and/or controllable valves, as known in the art. The flow direction of the dissolution medium is represented by the thin arrows immediately above the inflow 65 and outflow 75 tubing. A rocker assembly can rock the flow-through cell 10 to mimic the motion of saliva within the oral cavity. The rocker assembly in FIG. 1 comprises a rocker controller 80 to control rocking of flow-through cell 10 by rocker platform 85 connected to rocker controller 80 by support 82 and optionally temperature control 97. The rocking mimics the gentle swishing motion of saliva movement in the oral cavity and ensures uniform dispersal of the dissolved compound within cell 10. The arrows adjacent to rocker platform 85 represent the motion of rocker platform 85 and flow-through cell 10. A collection device 95 can be optionally connected downstream of the outlet port 40 for collecting samples of dissolution medium containing dissolved compound. This collection device can be stirred continuously to ensure complete mixing of the fluid and eliminate regional variations in concentration. Samples can then be analyzed by means known in the art to determine the concentration of dissolved compound. A filter 50 can be located upstream of the outflow tubing, including disposed within outlet port 40, to prevent collection of undissolved compound within efflux means.

In one embodiment, the dimensions of the device reflect the physical variables of solid dissolution in the oral cavity. That is, the volume of dissolution medium within the flow-through cell is similar to the volume of saliva within the oral cavity. Generally, this volume is less than approximately 100 mL, preferably between 0 and 75 mL, and more preferably between 25 mL and 50 mL for a device that models the human oral cavity. The inflow flow-rate can match typical saliva production in humans. However, saliva production rate varies depending on the age and health of the patient and whether saliva production has been stimulated. Unstimulated saliva glands can produce approximately 0.3 to 0.5 mL/min, and stimulated glands can produce between approximately 1 to 3 mL of saliva per minute. Users can control flow-rates through the flow-through cell, constrained only by the flow means employed (e.g. type of pump employed and size of model system). In one embodiment, flow-rates in the device can be varied from between 0 to 3 mL/min. In a preferred embodiment the flow-rate is between 0.9 mL/min and 1.1 mL/min, and more preferably 1 mL/min.

Those skilled in the art recognize that model systems can be suitably scaled using dimensionless correlations between the model system and the oral cavity system (the "in vivo system"). See, e.g. Fundamentals of Fluid Mechanics, Munson et al., (1990) pp. 401-463. For example, the solid compound volume to dissolution volume within the cell can have the same value in the model system and the in vivo system. Flow-rate can be similarly described with a dimensionless number (e.g. Reynolds number, Peclet number). In this manner, the invention encompasses a different size system, that is systems that are larger, systems that are smaller, and systems that have the same size as the oral cavity. In a preferred embodiment, the model system has dimensions and physical parameters similar to the in vivo oral cavity. In this manner, any mammal's oral cavity can be modeled by the device of the present invention.

In the oral cavity, solid dosages are exposed to saliva across all exposed dosage surfaces. Therefore, in a preferred embodiment, the solid dosage is placed on a compound holder 20 that is porous to permit dissolution medium to flow across all surfaces of the solid dosage. In one embodiment the mesh is in contact with the container bottom. The mesh is designed to simulate the porous/permeable absorptive surface of the mouth by allowing the dissolution medium to flow under the dosage form. In one embodiment, the mesh is size 60 and made of steel. In a preferred embodiment, the mesh is a non-reactive screen, including a non-reactive metal screen, and preferably a stainless steel metal screen. Generally, stainless steel is standard in laboratory settings and most suitable for this purpose. In an alternative embodiment, plastic or Teflon coated mesh may be used. However, the plastic or Teflon coated mesh differ in the interfacial tension they experience with aqueous media and may adversely affect passage of liquid through the mesh compared to an uncoated stainless steel mesh. The mesh size can be any mesh size that is suitable for a particular application, as known in the art. In a preferred embodiment, the mesh size can be between approximately 40 and approximately 200. As used herein, solid compound encompasses substances whose solubility within the oral cavity is to be tested and includes tablets, pills, powders, syrups, suspensions, mucoadhesives, bioadhesives and lozenges. The solid compound can be incorporated within mucoadhesives, as disclosed in Das & Das (2004), and the mucoadhesive placed on the compound holder.

Entry port 25 facilitates addition of solid compounds to the flow-through cell 10, as well as addition of dissolution medium to the flow through cell prior to initiating the flow experiment. In one embodiment, the flow-through cell is completely filled with dissolution medium so that no air pocket remains within the flow-through cell. Alternatively, the flow-through cell can be partially filled with dissolution medium such that a portion of the cell remains air filled. Entry port 25 can be sealingly engaged with cell 10 to minimize or prevent evaporation of dissolution medium. The seal can be provided by, for example, threaded screw, stopper or by a septum.

Because agitation of saliva in the mouth is generally minimal, the cell is preferably slowly and gently agitated at a fixed rate. A rocking motion is preferred to a stirring motion. Because the volume of dissolution medium in the cell preferably remains constant, the flow-rate of dissolution medium exiting the cell preferably equals the flow-rate of dissolution medium entering the cell. The exit flow-rate can be controlled by a separate pump downstream of the flow-through cell that pulls fluid from the cell. A separate pump up-stream from the flow-through cell can independently control the flow-rate of dissolution medium entering the flow-through cell. In a configuration wherein there is no air pocket contained within the flow-through cell, a single pump, either up-stream or down-stream of the flow-through cell can generate both inflow flow-rate and the outflow flow-rate, wherein inflow and outflow flow-rates are equal.

Alternatively, a pressure head can be used to drive fluid flow through the flow-through cell. A pressure head is generated by a difference in height between an inflow reservoir and an outflow reservoir, wherein the pressure head is calculated as: $\Delta P = \rho g h$, where $\Delta P$ is the pressure difference, $\rho$ is the fluid density, g is the local acceleration due to gravity and h is the height difference between the inflow and outflow reservoir. Flow-rate can be measured and/or controlled using a flowmeter. Pressure head-generated inflow and outflow is preferably used in the flow-through cell configuration wherein there is no air pocket within the cell. However, the flow-through cell can be partially filled, and left open to the atmosphere, so that there can be a separate head for driving inflow (height difference between inlet reservoir and medium within the flow-through cell) and driving outflow (height difference between medium within the flow-through cell and outlet reservoir). For the pressure head configurations, the surface area of the reservoirs exposed to atmosphere should be large so that change in reservoir height during flow is negligible. In addition, to minimize evaporation of dissolution medium the flow-through cell, exposure of the medium within the flow-through cell to atmosphere is minimized.

To prevent withdrawal of undissolved particles from the flow-through cell 10, a filter 50 can be disposed within the device. Preferably, the filter 50 is disposed immediately upstream of the outflow tubing 75 within the outlet port 40 and has a pore size less than 10 microns, more preferably between 0.25 microns and 5 microns. Entry of undissolved particles into outflow tubing 75 can be minimized by placing the outlet port 40 toward the top of the cell and placing the compound 15 and compound holder 20 toward the bottom of the cell, thereby permitting gravitational forces to minimize entry of undissolved particles into the outlet port 40. Such placement of outlet port 40 minimizes the likelihood of filter 50 clogging by undissolved particles. As used herein, prevention of undissolved compound from entering the efflux sink means an insignificant quantity of undissolved compound, relative to dissolved compound, is contained in the efflux sink. In one embodiment, such an amount is equal to less than 1% the amount of dissolved compound. No undissolved compound means no measurable quantity of undissolved compound is detected in the fluid within the outflow tubing 75 or outflow means.

As used herein, "influx source" refers to the volume of dissolution medium upstream of the flow-through cell. The influx source supplies medium to the flow through cell, and includes tubing used to deliver medium to the flow-through cell. "Efflux sink" is used herein to refer to a reservoir of dissolution medium that has passed through the flow-through cell. The efflux sink includes tubing downstream of the flow-through cell and an optional reservoir into which the tubing drains. A sample can be taken from the efflux sink to determine a solid compound's dissolution within the medium. In a preferred embodiment the inflow and efflux flow-rates are constant. The flow rate from the influx source can be variably controlled by an inflow flow-rate controlling device, and the flow rate of the efflux sink can be variably controlled by an efflux flow-rate controlling device. In one embodiment, a pump provides the means to variably control the flow-rate (see FIG. 1, flow rate controls 63 and 73). In another embodiment, variation of the height of the pressure head provides flow-rate control. Alternatively, a pressure head can provide flow-rate and a flow-meter can provide means to vary the flow-rate. "Variably control" refers to the user having the ability to vary the magnitude of the constant flow-rate of dissolution medium into and out of the flow-through cell.

The dissolution medium is preferably a simulated saliva. The composition of simulated saliva is known in the art and can be, for example, 2.38 g $Na_2HPO_4$, 0.19 g $KH_2PO_4$, 8 g NaCl in one liter of distilled water, adjusted with phosphoric acid to pH 6.75. Other simulated saliva compositions are disclosed in US Pub. No. 2003/0087457, herein specifically incorporated by reference for simulated saliva composition.

Because solubility is dependent upon temperature, the dissolution medium is kept at the temperature of saliva within the oral cavity. This is typically at a temperature of about 37° C. In a preferred embodiment the temperature of the influx source of dissolution medium is maintained at 37±2° C. and the temperature of the flow-through cell is maintained at 37±2° C. The rocker can include a temperature control 97. A temperature controlled rocker with controllable movement for gentle swirling of the dissolution medium in the flow-through cell can be utilized. Another heating unit can be used to control the temperature of the influx source. The heating unit can be any device known in the art, for example, a hot plate or it can be a water bath.

In a preferred embodiment, flexible tubing is connected to each of the inflow port 30 and outflow port 40 to facilitate rocking of cell 10 by rocker platform 85. The upstream end of the inflow tubing 65 is connected to a source of inflow fluid, such as an inlet reservoir 62, and the other downstream end of the outflow tubing 75 is connected to an efflux sink, such as an efflux reservoir 90. The efflux sink can also be a syringe pump's syringe cavity. A collection device can collect samples of dissolution medium containing dissolved compound. The samples can be collected continuously or, alternatively, intermittently, as necessary to obtain a drug content/concentration time course. The collection device is any means known in the art whereby a volume of fluid can be collected. The collection device can be connected to the efflux sink, or alternatively, upstream from the efflux sink and downstream from filter 50. The collection device can be passive collection of dissolution medium, for example, a stopcock 95 to redirect outflow to a collection container or a container to which the outflow tubing can be temporarily placed, or actively collecting medium by syringe withdrawal or by a pump. Alternatively, an in-line dissolution-measuring device can be disposed in the outflow tubing 75, as known in the art, including a spectrophotometer and other devices known in the art (see, e.g., U.S. Pat. Pub. No. 2003/008745), for in-line measurement of compound dissolution.

Pumps that provide constant and reliable flow-rates on the order of 1 mL/min are known in the art. Any pump that can provide a flow-rate in the range of 0 to approximately 3 mL/min are suitable for use in the present invention and include positive displacement, syringe, peristaltic, metering, diaphragm and dynamic pumps. Those of skill in the art recognize the particular type of pump to be used depends on a variety of factors including chemical compatibility, medium viscosity, temperature, flow rates and pressure, and can select an appropriate pump given the specific experimental conditions. Pressurized systems can also provide reliable flow-rates that can be controlled with valves, including flow-meters containing valves.

Figure 2A:
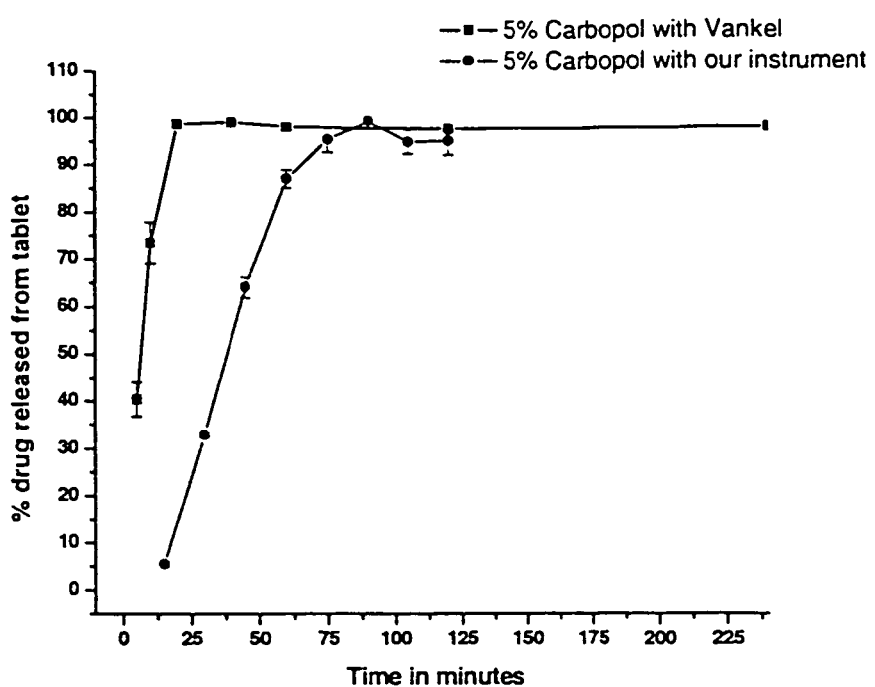
FIG. 2: Comparison of (FIG. 2A) percent drug release and (FIG. 2B) drug concentration as a function of time of a 5% Carbopol solid obtained from a Vankel instrument and an instrument of the present invention.
Figure 2B:
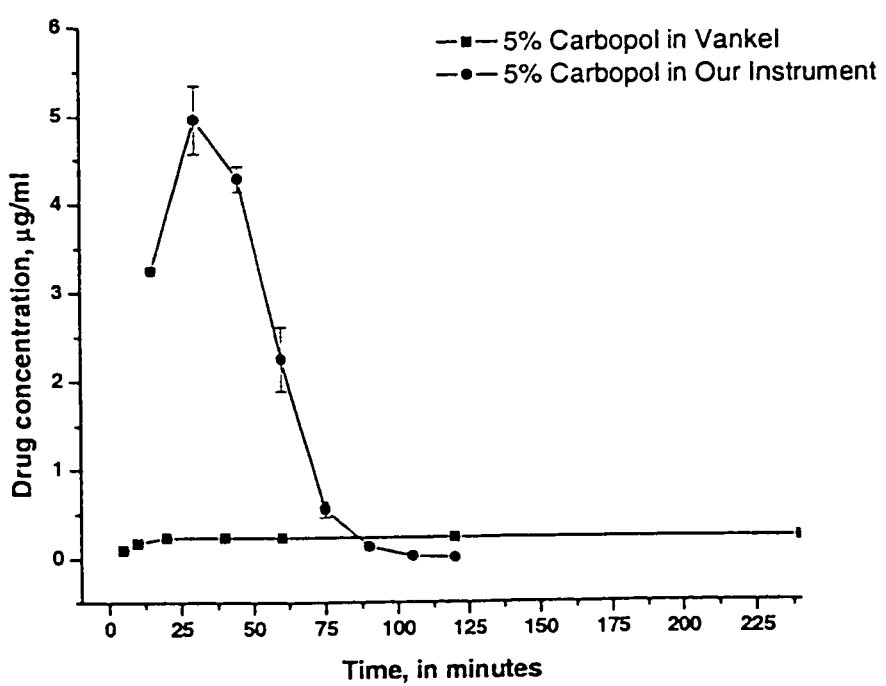

Dissolution Data. FIGS. 2A-B show representative dissolution data using the device of the present invention compared to dissolution data obtained from a Vankel device. The data show there are differences in dissolution for the initial 75 minutes of 5% CARBOPOL® (CARBOPOL® comprises a set of high molecular weight homo- and co-polymers of acrylic acid, crosslinked with a polyalkenyl polyether) between the device of the present invention and the Vankel device. FIG. 2A shows the cumulative amount of drug, expressed as a percentage, in the efflux reservoir 90 as a function of time. FIG. 2B shows drug 'concentration' in the flow cell 10 as a function of time. As is common for polymer-containing controlled release dosage forms, the rate of dissolution is rapid over the first few minutes as the polymer is initially exposed to fluid. After this initial exposure time, the rate of drug release slows. This is reflected in the initial spike in drug concentration in the flow cell 10 (see FIG. 2B) and the steep slope of drug release at early times (see FIG. 2A). Dissolved drug concentration measurements in the dissolution medium samples were performed on an HPLC system.

We claim:

1. A device for in vitro testing of dissolution of a solid compound, wherein said device models an oral cavity, said device comprising:
   (a) an influx source having an inflow flow-rate;
   (b) a flow-through cell connected to the influx source, said flow-through cell having a capacity for receiving a volume of dissolution medium and the solid compound;
   (c) a sample holder for receiving a solid compound, said sample holder connected to the flow-through cell;
   (d) an efflux sink having an efflux flow-rate, said efflux sink being connected to the flow-through cell, wherein the dissolution medium is introduced to the flow-through cell at the inflow flow-rate and the dissolution medium is removed from the flow-through cell at the efflux flow-rate;
   (e) a filter disposed between the flow-through cell and the efflux sink to prevent undissolved compound from entering the efflux sink; and
   (f) a temperature-controlled adjustable rocker-assembly operably connected to the flow-through cell to rock the flow-through cell at a user-controlled temperature
wherein dissolution medium flows over all surfaces of the solid compound on the sample holder.

2. The device of claim 1, wherein the influx source further comprises an inflow rate controlling device to variably control the inflow flow-rate of dissolution medium introduced to the flow-through cell.

3. The device of claim 2, wherein the efflux sink further comprises an efflux flow-rate controlling device to variably control the efflux flow-rate of the dissolution medium removed from the flow-through cell.

4. The device of claim 3, wherein the inflow flow-rate equals the efflux flow-rate.

5. The device of claim 4, wherein the inflow flow-rate is provided by a pump.

6. The device of claim 4, wherein the volume of dissolution medium in the flow-through cell is less than 100 mL.

7. The device of claim 6, wherein the influx flow-rate is less than 2 mL/min.

8. The device of claim 1, further comprising a collection device operably connected to the efflux sink to collect dissolution medium from the efflux sink for dissolution analysis.

9. A method for determining the dissolution of a solid compound comprising:
   (a) providing the apparatus of claim 1;
   (b) introducing the solid compound to the sample holder in the flow-through cell;

(c) supplying dissolution medium to the flow-through cell;
(d) collecting a sample of dissolution medium from the efflux sink; and
(e) analyzing the sample of dissolution medium to determine the amount of the dissolved compound in the sample.

10. The method of claim 9, further comprising repeatedly collecting and analyzing samples to obtain a dissolution time course of the solid compound.

11. The device of claim 1, further comprising:
(a) an inflow port connecting the flow-through cell and the influx source, wherein said inflow port is located at a position below the sample holder; and
(b) an outflow port connecting the flow-through cell and the efflux sink, wherein said outflow port is located at a position above the sample holder.

12. A device for evaluating dissolution of a compound wherein said device models an oral cavity, said device comprising:
(a) a flow-through cell for receiving a volume of dissolution medium and a compound comprising:
(i) an inflow port;
(ii) an outflow port;
(iii) a compound holder, wherein the compound holder facilitates flow of the dissolution medium over all surfaces of the solid compound on the holder;
(b) inflow means connected to the inflow port for introducing the dissolution medium to the flow-through cell;
(c) outflow means connected to the outflow port for removing the dissolution medium from the flow-through cell, wherein the removed dissolution medium does not contain undissolved test compound; and
(d) a rocker assembly operably connected to the flow-through cell for dispersing dissolved compound throughout the dissolution medium disposed within the flow-through cell.

13. The device of claim 12, further comprising a collection device connected to the outflow means.

14. The device of claim 12, further comprising an in-line filter disposed within the outflow port to prevent undissolved particles from being removed from the flow-through cell.

15. The device of claim 12, further comprising a temperature controlled assembly operably connected to the flow-through cell.

16. The device of claim 12, further comprising a temperature controlled influx source operably connected to the inflow means.

17. The device of claim 12, wherein the volume of dissolution medium within the flow-through cell is between 35 mL and 75 mL.

18. The device of claim 17, wherein the dissolution medium is simulated saliva.

19. The device of claim 12, wherein the inflow port is positioned below the compound holder and the outflow port is positioned above the compound holder.

* * * * *